United States Patent
Ren et al.

(10) Patent No.: US 10,209,238 B2
(45) Date of Patent: Feb. 19, 2019

(54) SMART TOILET, OPERATION CONTROL METHOD AND OPERATION CONTROL DEVICE OF SMART TOILET

(71) Applicant: BOE Technology Group Co., Ltd., Beijing (CN)

(72) Inventors: Yan Ren, Beijing (CN); Xiao Zhang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 0 days.

(21) Appl. No.: 15/745,022

(22) PCT Filed: Jul. 7, 2017

(86) PCT No.: PCT/CN2017/092133
§ 371 (c)(1),
(2) Date: Jan. 15, 2018

(87) PCT Pub. No.: WO2018/024077
PCT Pub. Date: Feb. 8, 2018

(65) Prior Publication Data
US 2019/0011425 A1 Jan. 10, 2019

(30) Foreign Application Priority Data
Aug. 5, 2016 (CN) .......................... 2016 1 0634454

(51) Int. Cl.
*G01N 33/493* (2006.01)
*G01N 35/10* (2006.01)
(Continued)

(52) U.S. Cl.
CPC ......... *G01N 33/493* (2013.01); *A61B 10/007* (2013.01); *E03D 9/00* (2013.01);
(Continued)

(58) Field of Classification Search
CPC .............. A61B 10/007; A61B 10/0038; A61B 5/14532; A61B 5/14546; C12Q 1/54;
(Continued)

(56) References Cited

U.S. PATENT DOCUMENTS 3,478,690 A * 11/1969 Helke ....................... F04D 3/00
210/380.1
4,131,959 A * 1/1979 Albertassi ............... E03D 11/11
4/319
(Continued)

FOREIGN PATENT DOCUMENTS

| CN | 104452926 A | 3/2015 |
| CN | 104499547 A | 4/2015 |

(Continued)

OTHER PUBLICATIONS

Oct. 13, 2017—International Search Report and Written Opinion Appn PCT/CN2017/092133 with Eng Tran.

*Primary Examiner* — David J. McCrosky
(74) *Attorney, Agent, or Firm* — Banner & Witcoff, Ltd.

(57) ABSTRACT

A smart toilet includes: a toilet body; a urine cup disposed outside the toilet body; a urine collection device disposed in the toilet body, including a rotation shaft and a front urine storage cup, a middle urine storage cup and a rear urine storage cup distributed around the rotation shaft, the front urine storage cup is provided with a first urine detection sensor and a first valve, the middle urine storage cup is provided with a second urine detection sensor and a second valve; a drive motor, connected with the rotation shaft; a controller, configured to control the drive motor to drive the rear urine storage cup to rotate to the urine collection position and control the second valve to be turned on upon urine volume in the middle storage cup reaching a volume (Continued)

threshold. An operation control method and device of a smart toilet are also provided.

12 Claims, 5 Drawing Sheets

(51) Int. Cl.
*E03D 11/11* (2006.01)
*E03D 11/13* (2006.01)
*A61B 10/00* (2006.01)
*E03D 9/00* (2006.01)
*G01N 33/50* (2006.01)

(52) U.S. Cl.
CPC .............. *E03D 11/11* (2013.01); *E03D 11/13* (2013.01); *G01N 35/10* (2013.01); *G01N 33/50* (2013.01)

(58) Field of Classification Search
CPC ...... C12Q 1/006; Y10S 435/97; G01N 33/493; G01N 33/50; G01N 35/10; G01N 33/528; E03D 9/00; E03D 11/11; E03D 11/13; E03D 11/00; Y10T 436/118339; Y10T 436/25

See application file for complete search history.

(56) References Cited

U.S. PATENT DOCUMENTS

| | | | | |
|---|---|---|---|---|
| 4,860,767 | A * | 8/1989 | Maekawa | E03D 11/00 600/573 |
| 5,068,926 | A * | 12/1991 | Suzuki | E03D 11/11 4/318 |
| 5,198,192 | A * | 3/1993 | Saito | A61B 5/14532 4/314 |
| 7,195,602 | B2 * | 3/2007 | Yong | A61B 10/007 600/573 |
| 8,367,000 | B2 * | 2/2013 | Yano | G01N 1/4077 422/500 |
| 9,974,520 | B2 * | 5/2018 | Kramer | A61B 10/007 |
| 2018/0055489 | A1 * | 3/2018 | Kramer | A61B 10/007 |

FOREIGN PATENT DOCUMENTS

| | | | |
|---|---|---|---|
| CN | 104746618 A | 7/2015 | |
| CN | 105136798 A * | 12/2015 | ............... E03D 9/00 |
| CN | 205670096 U | 11/2016 | |
| CN | 106193230 A | 12/2016 | |
| JP | 2000-088845 A | 3/2000 | |
| KR | 10-1080828 B1 | 11/2011 | |

* cited by examiner

SMART TOILET, OPERATION CONTROL METHOD AND OPERATION CONTROL DEVICE OF SMART TOILET

The application is a U.S. National Phase Entry of International Application No. PCT/CN2017/092133 filed on Jul. 7, 2017, designating the United States of America and claiming priority to Chinese Patent Application No. 201610634454.3 filed Aug. 5, 2016. The present application claims priority to and the benefit of the above-identified applications and the above-identified applications are incorporated by reference herein in their entirety.

TECHNICAL FIELD

At least one embodiment of the present disclosure relates to a smart toilet, an operation control method and an operation control device of a smart toilet.

BACKGROUND

Currently, as a pace of people's life is getting faster and faster, work pressure is getting greater and greater, and the health problem is also getting more and more attention of people. A regular physical examination may help people to understand more about their own health. Urine examination is the most basic items in the physical examination projection, and a general procedure for a patient to go to a hospital for the urine examination is: taking a container from a designated place according to a slip write out by a doctor, and taking a urine sample in a bathroom, and then setting the urine simple to a staff member who collect simples to test. Therefore, a hospital needs to arrange for a dedicated staff member to manage containers for collecting urine samples and intensively collecting the urine samples of patients.

A drawback of the prior art is that in a procedure of the urine examination as mentioned above, the patient needs to collect the urine sample by himself, which is more inconvenient to operate and poor health. In addition, a standard urine simple is middle urine, so as to ensure the accuracy of the examination result; however, a patient is difficult to obtain the middle urine accurately in a sampling process, which is also resulted to an error of the examination result.

SUMMARY

An object of embodiments of the present disclosure is to provide a smart toilet, an operation control method and an operation control device of a smart toilet, so as to collect a urine detection sample accurately and improve convenience and health of a urine collection.

An embodiment of the present disclosure provides a smart toilet, which includes: a toilet body; a urine cup disposed outside the toilet body; a urine collection device disposed in the toilet body, which includes a rotation shaft and a urine storage container driven to be rotated by the rotation shaft, the urine storage container includes a front urine storage cup, a middle urine storage cup and a rear urine storage cup distributed around the rotation shaft, the front urine storage cup is provided with a first urine detection sensor and a first valve, the middle urine storage cup is provided with a second urine detection sensor and a second valve; the front urine storage cup and the rear urine storage cup are connected with a catheterization pipeline of the smart toilet, the middle urine storage cup is connected with the urine cup through a pipeline; a drive motor, being in drive connection with the rotation shaft; a controller, electrically connected with the first urine detection sensor, the first valve, the second urine detection sensor, the second valve and the drive motor, and configured to control the drive motor to drive the middle urine storage cup to rotate to a urine collection position upon urine volume in the front urine storage cup reaching a first urine volume threshold; control the drive motor to drive the rear urine storage cup to rotate to the urine collection position and control the second valve to be turned on upon urine volume in the middle storage cup reaching a second urine volume threshold.

In the smart toilet provided by an embodiment of the present disclosure, through controlling the drive motor to drive the urine storage container to rotate, so as to make the front urine storage cup, the middle urine storage cup and the rare urine storage cup locate in the urine collection position in turn and collect front urine, middle urine and rare urine respectively, and turning on the second valve to transfer the middle urine into the urine cup as a urine detection sample for testing. Comparing with the prior art, the technical solution can collect the middle urine as the urine detection sample accurately, and improve convenience and health of the urine collection.

For example, in the smart toilet provided by an example of the present disclosure, the first urine detection sensor and the first valve is provided at a bottom of the front urine storage cup, the second urine detection sensor and the second valve are provided at a bottom of the middle urine storage cup.

For example, in the smart toilet provided by an example of the present disclosure, the smart toilet further includes an accommodating barrel and a funnel-shaped catheterization plate having a leak hole and located on a top of the accommodating barrel, the urine collection device and the drive motor are located in the accommodating barrel, a position below the leak hole of the catheterization plate is the urine collection position. In the present technical solution, the catheterization plate may gather urine and make the urine accurately flow through the leak hole into the front urine storage cup, the middle urine storage cup and the rare urine storage cup in turn, so as to reduce a probability of urine splashing to collect the urine sample more accurately.

For example, in the smart toilet provided by an example of the present disclosure, the smart toilet further includes a block wall barrel located outside the accommodating barrel and spaced from the accommodating barrel, a linear motor configured to drive the accommodating barrel to move up and down and an information collection device configured to collect patient identity information, the controller is electrically connected with the linear motor and the information collection device, and configured to control the linear motor to drive the accommodating barrel to move downward until the catheterization plate is in contact with an upper end surface of the block wall barrel upon receiving the patient identity information. In the present technical solution, in a case that the controller dose not receive the patient identity information, the smart toilet may be used as a normal toilet, the urine may flow through a gap between the catheterization plate and the upper end surface of the block wall barrel into the catheterization pipeline between the accommodating barrel and the block wall barrel and be drained away; in a case that the controller receives the patient identity information, the linear motor is controlled to drive the accommodating barrel to move downward until the catheterization plate is in contact with the upper end surface of the block wall barrel, the urine flows into the front urine storage cup, the middle urine storage cup and the rare urine storage cup in turn through the gather role of the catheterization plate, so as to collect the middle urine as the urine detection sample accurately. Therefore, the technical solution expands the application of the smart toilet and improves the usability of the smart toilet.

For example, in the smart toilet provided by an example of the present disclosure, a position of the catheterization plate opposed to the upper end surface of the blocking wall barrel is provided with a seal strip. The seal strip is capable of improving sealing performance between the catheterization plate and the block wall barrel, and preventing the urine from flowing into the catheterization pipeline between the accommodating barrel and the block wall barrel through the gap between the catheterization plate and the upper end surface of the block wall barrel and draining out during the urine collection.

For example, in the smart toilet provided by an example of the present disclosure, the smart toilet further includes a cleaning device configured to wash an interior of the toilet body, the controller is electrically connected with the cleaning device, and configured to turn on the cleaning device upon rare urine collection being completed. Residual urine of a patient may be cleaned by using the cleaning device to wash and disinfect the interior of the smart toilet, so as to reduce influence on urine samples collected by other patients who use the smart toilet, thereby collecting the urine samples more accurately.

The present disclosure further provides an operation control method of any of the smart toilets as mentioned above, includes: obtaining front urine volume in the front urine storage cup detected by the first urine detection sensor; when the front urine volume reaches the first urine volume threshold, controlling the drive motor to drive the middle urine storage cup to rotate to the urine collection position; obtaining middle urine volume in the middle urine storage cup detected by the second urine detection sensor; when the middle urine volume reaches the second urine volume threshold, controlling the drive motor to drive the rear urine storage cup to rotate to the urine collection position and controlling the second valve to be turned on.

In the operation control method of the smart toilet provided by the present disclosure, through controlling the drive motor to drive the urine storage container to rotate, so as to make the front urine storage cup, the middle urine storage cup and the rare urine storage cup locate in the urine collection position in turn and collect front urine, middle urine and rare urine respectively, and turning on the second valve to transfer the middle urine into the urine cup as a urine detection sample for testing. Comparing with the prior art, the technical solution can collect the middle urine as the urine detection sample accurately, and improve convenience and health of the urine collection.

For example, in the operation control method of the smart toilet provided by an example of the present disclosure, the operation control method of the smart toilet further includes: when receiving the patient identity information, controlling the linear motor to drive the accommodating barrel to move downward until the catheterization plate is in contact with the upper end surface of the block wall barrel.

For example, in the operation control method of the smart toilet provided by an example of the present disclosure, the operation control method of the smart toilet further includes: when the rare urine collection is completed, turning on the cleaning device so as to wash the interior of the toilet body.

The present disclosure further provides an operation control device of any one of the smart toilets as mentioned above, which includes: an obtaining unit, configured to obtain front urine volume detected by the first urine detection sensor and middle urine volume detected by the second urine detection sensor; a control unit, configured to control the drive motor to drive the middle urine storage cup to rotate to the urine collection position when front urine volume in the first urine storage cup reaches the first urine volume threshold; control the drive motor to drive the rear urine storage cup to rotate to the urine collection position and control the second valve to be turned on when middle urine volume in the middle urine storage cup reaches the second urine volume threshold.

In the operation control device of the smart toilet provided by the present disclosure, through controlling the drive motor to drive the urine storage container to rotate, so as to make the front urine storage cup, the middle urine storage cup and the rare urine storage cup locate in the urine collection position in turn and collect front urine, middle urine and rare urine respectively, and turning on the second valve to transfer the middle urine into the urine cup as a urine detection sample for testing. Comparing with the prior art, the technical solution can collect the middle urine as the urine detection sample accurately, and improve convenience and health of the urine collection.

For example, in the operation control device of the smart toilet provided by an example of the present disclosure, the control unit is configured to control the linear motor to drive the accommodating barrel to move downward until the catheterization plate is in contact with the upper end surface of the block wall barrel when receiving the patient identity information.

For example, in the operation control device of the smart toilet provided by an example of the present disclosure, the control unit is configured to turn on the cleaning device so as to wash the interior of the toilet body when the rare urine collection is completed.

BRIEF DESCRIPTION OF THE DRAWINGS

In order to clearly illustrate the technical solution of embodiments of the present disclosure, the drawings of the embodiments or related technical description will be briefly described in the following; it is obvious that the drawings in the description are only related to some embodiments of the present disclosure and not limited to the present disclosure.

REFERENCE NUMERALS

1—toilet body; 10—urine cup; 20—urine collection device; 21—urine storage container; 211—front urine storage cup; 212—middle urine storage cup; 213—rare urine storage cup; 214—first valve; 215—second valve; 216— first urine detection sensor; 217—second urine detection sensor; 22—rotate shaft; 23—catheterization pipeline; 24—pipeline; 30—drive motor; 31—controller; 40—accommodating barrel; 50—catheterization plate; 51—leak hole; 52—seal strip; 60—block wall barrel; 70—linear motor; 80—information collection device; 90—cleaning device; 100—obtaining unit; 200—control unit.

DETAILED DESCRIPTION

In order to make objects, technical details and advantages of the embodiments of the present disclosure apparent, the technical solutions of the embodiments will be described in a clearly and fully understandable way in connection with the drawings related to the embodiments of the disclosure. It is obvious that the described embodiments are just a part but not all of the embodiments of the disclosure. Based on the described embodiments herein, a person having ordinary skill in the art can obtain other embodiment(s), without any inventive work, which should be within the scope of the disclosure.

In order to collect a urine detection sample accurately, and improve convenience and health of urine collection, the present disclosure provides a smart toilet, an operation control method and an operation control device of a smart toilet. In order to make objects, technical details and advantages of the embodiments of the present disclosure apparent, the present disclosure will be described in detail by the following examples.

Figure 1:
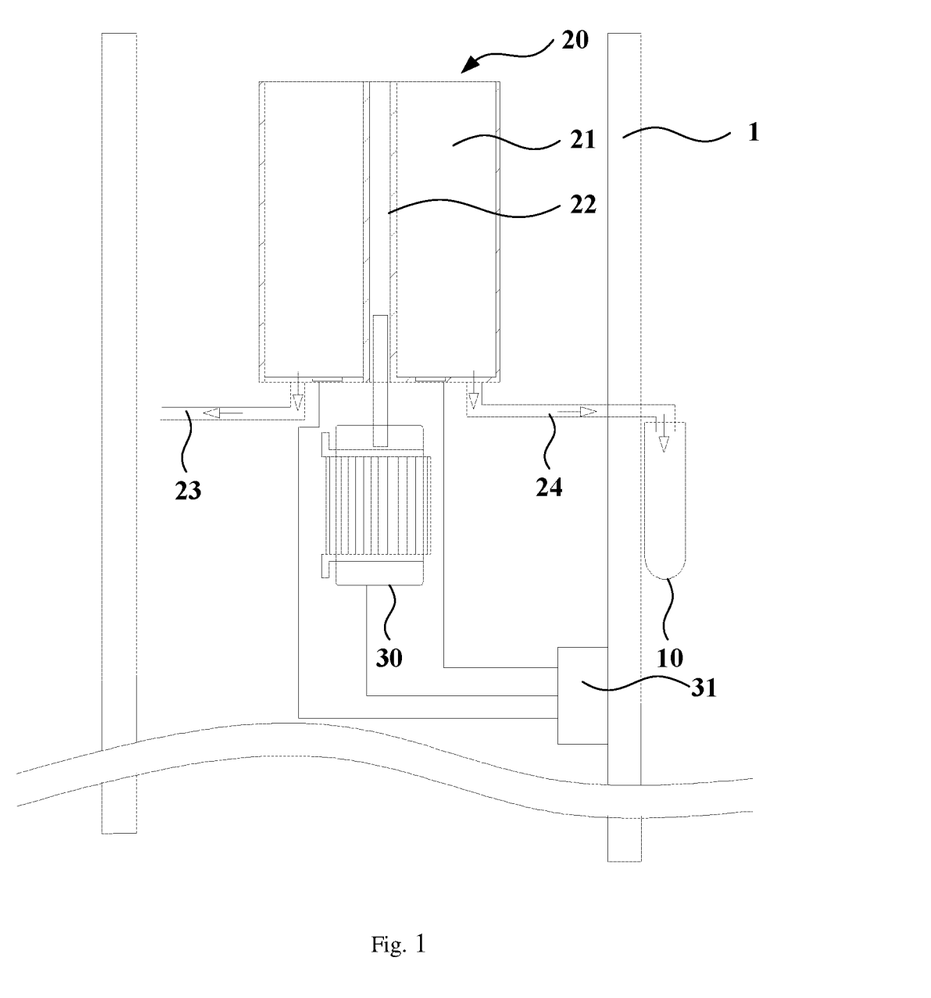
FIG. 1 is a partial structure view of a smart toilet provided by an embodiment of the present disclosure.
Figure 2:
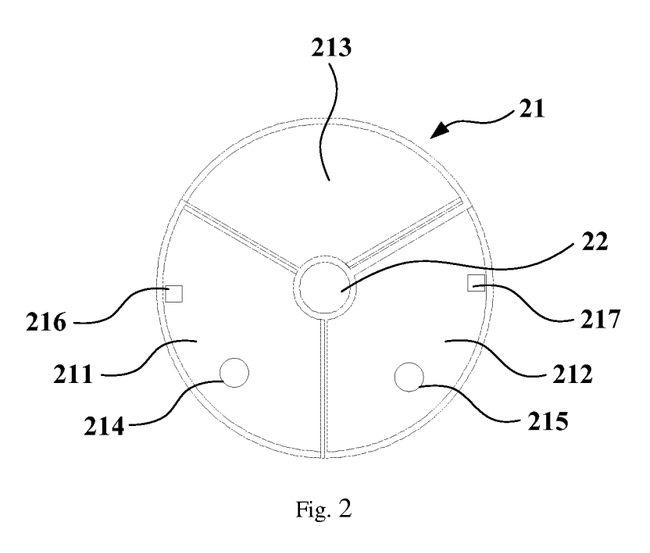
FIG. 2 is a planer structure view of a urine storage container provided by an embodiment of the present disclosure.

FIG. 1 is a partial structure view of a smart toilet provided by an embodiment of the present disclosure, and FIG. 2 is a planar structure view of a urine storage container provided by an embodiment of the present disclosure. As illustrated in FIG. 1 and FIG. 2, a smart toilet provided by an embodiment of the present disclosure includes: a toilet body 1; a urine cup 10 disposed outside the toilet body 1; a urine collection device 20 disposed in the toilet body 1, which includes a rotation shaft 22 and a urine storage container 21 driven to be rotated by the rotation shaft, the urine storage container 21 includes a front urine storage cup 211, a middle urine storage cup 212 and a rear urine storage cup 213 distributed around the rotation shaft 22, the front urine storage cup 211 is provided with a first urine detection sensor 216 and a first valve 214, the middle urine storage cup 212 is provided with a second urine detection sensor 217 and a second valve 215; the front urine storage cup 211 and the rear urine storage cup 213 are connected with a catheterization pipeline 23 of the smart toilet, the middle urine storage cup 212 is connected with the urine cup 10 through a pipeline 24; a drive motor 30, being in drive connection with the rotation shaft 22, the drive motor 30 controls the rotate shaft 22 to rotate to drive the urine storage container 21 to rotate; a controller 31, electrically connected with the first urine detection sensor 216, the first valve 214, the second urine detection sensor 217, the second valve 215 and the drive motor 30, and configured to control the drive motor 30 to drive the middle urine storage cup 212 to rotate to a urine collection position when urine volume in the front urine storage cup 211 reaches a first urine volume threshold; control the drive motor 30 to drive the rear urine storage cup 213 to rotate to the urine collection position and control the second valve 215 to be turned on when urine volume in the middle storage cup 212 reaches a second urine volume threshold. After the second valve 215 is turned on, the middle urine in the middle urine storage cup 212 is transferred to the urine cup 24 through the pipeline 24 for subsequent detection.

In the smart toilet provided by an embodiment of the present disclosure, through controlling the drive motor 30 to drive the urine storage container 21 to rotate, so as to make the front urine storage cup 211, the middle urine storage cup 212 and the rare urine storage cup 213 locate in the urine collection position in turn and collect front urine, middle urine and rare urine respectively, and transferring the middle urine into the urine cup 10 as a urine detection sample for testing. Comparing with the prior art, the technical solution can collect the middle urine as the urine detection sample accurately, and improve convenience and health of the urine collection.

For example, as illustrated in FIG. 2, the front urine storage cup 211 is provided with the first urine detection sensor 216 and the first valve 214, for example, a bottom or a side wall of the front urine storage cup 211 is provided with the first urine detection sensor 216 and the first valve 214. The middle urine storage cup 212 is provided with the second urine detection sensor 217, for example, a bottom and a side wall of the middle urine storage cup 212 is provided with the second urine detection sensor 217 and the second valve 215, the present embodiment is not limited thereto.

For example, when urine volume of the middle urine storage cup 212 reaches the second urine volume threshold, the drive motor 30 drives the rare urine storage cup 213 to rotate to the urine collection position, at this moment, the second valve 215 in the middle urine storage cup 212 rotates to a position opposed to the pipeline 24, and the second valve 215 is controlled to turn on so that the middle urine flows into the pipeline 24 and is transferred to the urine cup 10 as the urine detection sample, the present embodiment includes but is not limited thereto.

For example, the outside of the urine storage container may further be provided with a shell having a side wall and a bottom plate, the side wall or the bottom plate of the shell is provided with a connection port to be fixedly connected with the pipeline and the catheterization pipeline, the urine in the urine storage container may flow into the pipeline and the catheterization pipeline through the connection port, the present embodiment includes but is not limited thereto.

For example, opening time of the first valve 214 is not specifically limited in the present embodiment, when the urine volume in the front urine storage cup 211 reaches the first volume threshold, the controller 31 controls the drive motor 30 to drive the middle urine storage cup 212 to rotate to the urine collection position, and simultaneously controls the first valve 214 to be turned on, so that the urine in the front urine storage cup 211 is drained to the catheterization pipeline 23; or, the controller 31 pre-setting a catheterization time, when the catheterization time is reached, the first valve 214 is controlled to be turned on, so that the urine in the front urine storage cup 211 is drained to the catheterization pipeline 23.

For example, the rare urine storage cup 213 is not provided with an on-off valve, the urine is directly drained to the catheterization pipeline 23 in a case that the urine flows into the rare urine storage cup 213. For example, a bottom of the rare urine storage cup may be provided with a hole (which is not illustrated in FIG. 2), a position under the hole is aligned to the catheterization pipeline, so that the urine may be directly drained to the catheterization pipeline, the present embodiment includes but is not limited thereto.

For example, the urine cup 10 containing the urine detection sample may be sent to a urine detection position by a patient himself, may also be sent to the urine detection position by a special conveying equipment, such as a manipulator, conveyor belt and so on, which is not repeated thereto.

For example, specific capacity of the front urine storage cup 211, the middle urine storage cup 212 and the rare urine storage cup 213 is not limited, for example, according to that average capacity of a human bladder is 300 ml, the capacity of the front urine storage cup 211, the middle urine storage cup 212 and the rare storage cup 213 may be set to be 100 ml respectively. The first urine volume threshold in the present embodiment may be set according to experience so as to ensure collect the middle urine accurately, and the second urine threshold may be set according to urine volume of the urine sample prescribed by a hospital to meet a urine testing requirement.

It should be noted that, FIG. 1 only schematically illustrates a position of the controller 31, and its specific position may be set according to an actual situation, the present embodiment is not limited thereto. In addition, a collection line between the controller 31 and the drive motor 30 and other components indicates an electrical connection.

Figure 3:
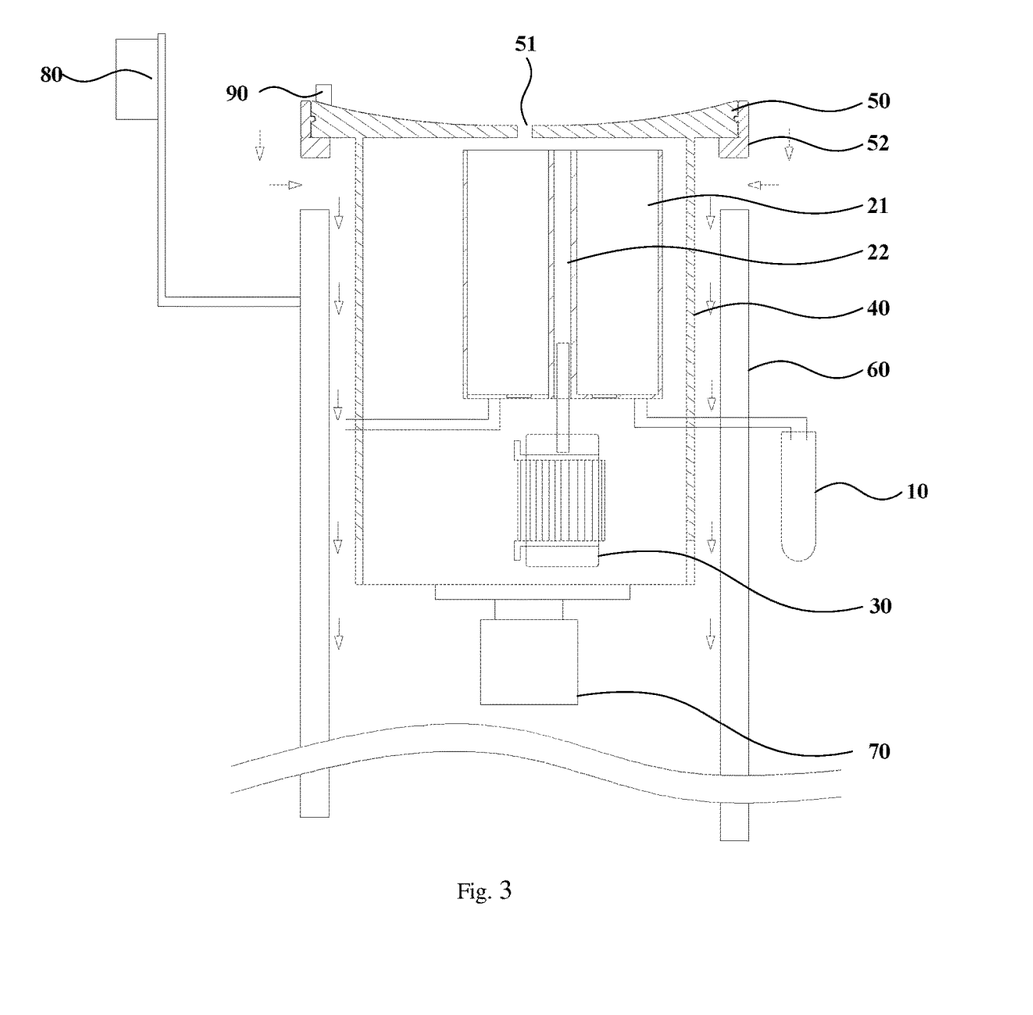
FIG. 3 is a partial structure view of a smart toilet when it does not collect urine provided by an embodiment of the present disclosure.

For example, FIG. 3 is a partial structure view of the smart toilet when it does not collect urine provided by an embodiment of the present disclosure, as illustrated in FIG. 3, in an embodiment of the present disclosure, the smart toilet further includes an accommodating barrel 40 and a funnel-shaped catheterization plate 50 having a leak hole 51 located on a top of the accommodating barrel 40. For example, the accommodating barrel 40 includes a bottom plate and a side wall around the bottom plate, a side of the side wall far away from the bottom plate is provided with the catheterization plate 50 having the leak hole 51, along an extending direction of the leak hole 51 to periphery of the leak hole 51, a distance between the catheterization plate 50 and the bottom plate gradually increases to form a funnel shape.

For example, as illustrated in FIG. 3, the urine collection device 21 and the drive motor 30 are located in the accommodating barrel 40, a position below the leak hole 51 of the catheterization plate 50 is the urine collection position. According to the present technical solution, the catheterization plate 50 may gather the urine and make the urine accurately flow into the front urine storage cup, the middle urine storage cup and the rare urine storage cup in turn through the leak hole 51 to reduce a probability of urine splashing to collect the urine sample more accurately.

Figure 4:
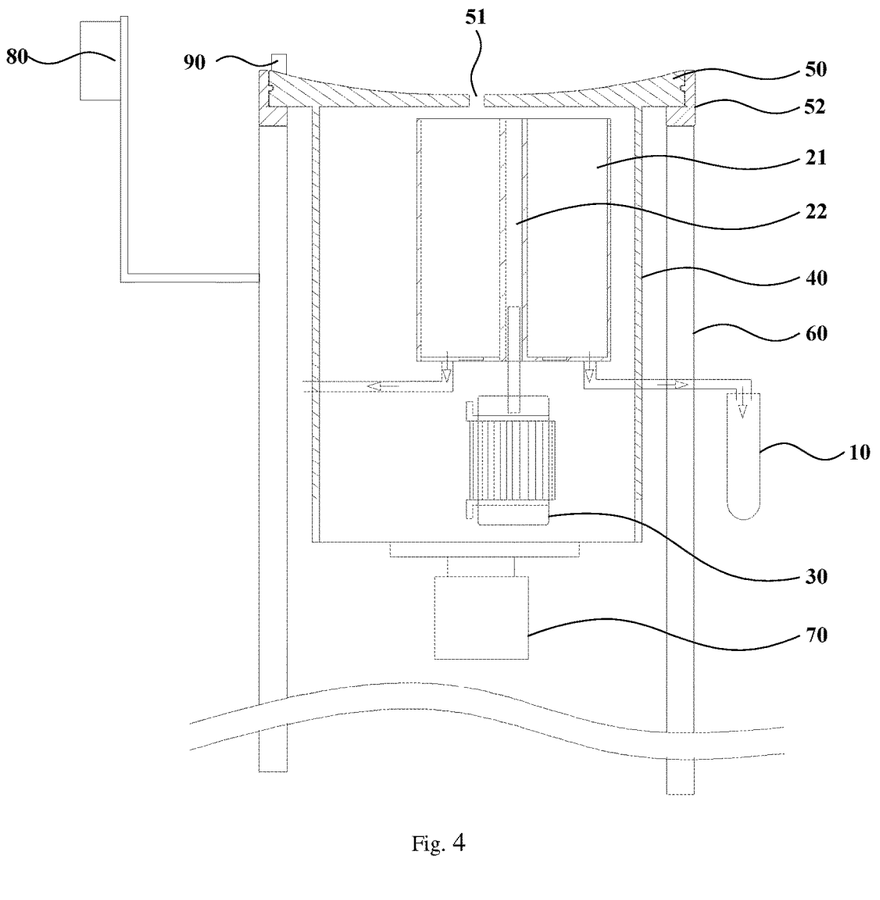
FIG. 4 is a partial structure view of a smart toilet when it collects urine provided by an embodiment of the present disclosure.

For example, FIG. 4 is a partial structure view of a smart toilet when it collects urine provided by an embodiment of the present disclosure, as illustrated in FIG. 3 and FIG. 4, the smart toilet further includes a block wall barrel 60 located outside the accommodating barrel 40 and spaced from the accommodating barrel 40, a linear motor 70 configured to drive the accommodating barrel 40 to move up and down and an information collection device 80 configured to collect patient identity information. Herein, "a block wall barrel 60 located outside the accommodating barrel 40 and spaced from the accommodating barrel 40" means that the accommodating barrel 40 is disposed inside the block wall barrel 60, and there is a distance between a barrel wall of the block wall barrel 60 and a barrel wall of the accommodating barrel 40, there is a distance between a bottom plate of the block wall barrel 60 and a bottom plate of the accommodating barrel 40.

For example, the controller (which is not illustrated in FIG. 4) is electrically connected with the linear motor 70 and the information collection device 80, and configured to control the linear motor 70 to drive the accommodating barrel 40 to move downward until the catheterization plate 50 is in contact with an upper end surface of the block wall barrel 60, that is, the linear motor 70 is controlled to drive the accommodating barrel 40 to move downward until the catheterization plate 50 is in contact with the upper end surface of the barrel wall of the block wall barrel 60 when receiving the patient identity information. In the present technical solution, in a case that the controller dose not receive the patient identity information, the catheterization plate 50 is not in connect with the upper end surface of the block wall barrel 60, therefore, the smart toilet may be used as a normal toilet, the urine may flow through a gap between the catheterization plate 50 and the upper end surface of the block wall barrel 60 into the catheterization pipeline between the accommodating barrel 40 and the block wall barrel 60 and be drained away, that is, the urine may flow through the gap below the catheterization plate 50 into the catheterization pipeline between the accommodating barrel 40 and the block wall barrel 60, and the urine cannot flow into the urine storage container 21 through the leak hole 51; in a case that the controller receives the patient identity information, the linear motor 70 is controlled to drive the accommodating barrel 40 to move downward until the catheterization plate 50 is in contact with the upper end surface of the barrel wall of the block wall barrel 60, the urine flows into the front urine storage cup, the middle urine storage cup and the rare urine storage cup in turn through the leak hole 51 under the gather role of the catheterization plate 50, so as to collect the middle urine as the urine detection sample accurately. Therefore, the technical solution expands the application of the smart toilet and improves the usability of the smart toilet.

For example, a specific type of the information collection device 80 is not limited, and may be a scanning device such as a barcode or a two-dimensional code scanner to achieve the patient identity information by collecting the barcode or the two-dimensional code and so on in a laboratory test of a patient. It should be noted that, FIG. 3 and FIG. 4 only schematically illustrate a position of the information collection device 80, a specific position of the information collection device may be set by an actual condition, the present embodiment is not limited thereto.

For example, a position of the catheterization plate 50 opposed to the upper end surface of the blocking wall barrel 60 is provided with a seal strip 52, that is, the catheterization plate 50 and the upper end surface of the barrel wall of the block wall barrel 60 are in a sealed junction with each other by the seal strip 52. The seal strip 52 is capable of improving sealing performance between the catheterization plate 50 and the block wall barrel 60, and preventing the urine from flowing into the catheterization pipeline between the accommodating barrel 40 and the block wall barrel 60 through the gap between the catheterization plate 50 and the upper end surface of the barrel wall of the block wall barrel 60 during the urine collection.

For example, in an example of the present disclosure, the smart toilet further includes a cleaning device 90 configured to wash an interior of the toilet body, the controller is electrically connected with the cleaning device 90, and configured to turn on the cleaning device 90 when rare urine collection is completed. Residual urine of a patient may be cleaned by using the cleaning device in the present embodiment to wash and disinfect the interior of the smart toilet, so as to reduce influence on urine samples collected by other patients who use the smart toilet, thereby collecting the urine samples more accurately. It should be noted that, FIG. 3 and FIG. 4 schematically illustrate a position of the cleaning device 90, and a specific position of the cleaning device 90 may be set according to an actual condition.

For example, in the present embodiment, when washing and disinfecting the interior of the toilet body, disinfectant passes through the catheterization plate and the urine storage container in turn, and drained away through the pipeline and the catheterization pipeline. In a process of washing and disinfecting, the controller may control the urine storage container to rotate and control the first valve and the second valve to be turned on and off according to a preset washing time, so as to fully wash and disinfect the interior of the toilet body.

An embodiment of the present disclosure further provides an operation control method of the smart toilet as mentioned in above embodiments, mainly includes:

obtaining front urine volume;

when the front urine volume reaches the first urine volume threshold, preparing for obtaining middle urine volume;

when the middle urine volume obtained reaches the second urine volume threshold, transferring the middle urine to the urine cup.

For example, the operation control method of the smart toilet provided by the present disclosure mainly includes:

obtaining the front urine volume in the front urine storage cup detected by the first urine detection sensor;

when the front urine volume reaches the first urine volume threshold, the drive motor is controlled to drive the middle urine storage cup to rotate to the urine collection position;

obtaining the middle urine volume in the middle urine storage cup detected by the second urine detection sensor;

when the middle urine volume reaches the second urine volume threshold, controlling the drive motor to drive the rear urine storage cup to rotate to the urine collection position and controlling the second valve to be turned on.

In the operation control method of the smart toilet provided by the present disclosure, through controlling the drive motor to drive the urine storage container to rotate, so as to make the front urine storage cup, the middle urine storage cup and the rare urine storage cup locate in the urine collection position in turn and collect front urine, middle urine and rare urine respectively, and turning on the second valve to transfer the middle urine into the urine cup as a urine detection sample for testing. Comparing with the prior art, the technical solution can collect the middle urine as the urine detection sample accurately, and improve convenience and health of the urine collection.

For example, opening time of the first valve is not specifically limited in the operation control method of the smart toilet provided by the present embodiment, when the front urine volume in the front urine storage cup reaches the first volume threshold, the drive motor is controlled to drive the middle urine storage cup to rotate to the urine collection position, and simultaneously the first valve is controlled to be turned on, so that the front urine in the front urine storage cup is drained to the catheterization pipeline; or, pre-setting a catheterization time, when the catheterization time is reached, the first valve 214 is controlled to be turned on, so that the front urine in the front urine storage cup is drained to the catheterization pipeline, the present embodiment includes but is not limited thereto.

For example, the operation control method of the smart toilet provided by an example of the present disclosure further includes:

when receiving the patient identity information, controlling the linear motor to drive the accommodating barrel to move downward until the catheterization plate is in contact with an upper end surface of the block wall barrel, the urine flows into the front urine storage cup, the middle urine storage cup and the rare urine storage cup in turn through the leak hole by the gather role of the catheterization plate, so as to collect the middle urine as the urine detection sample accurately.

For example, the operation control method of the smart toilet provided by an example of the present disclosure, further includes:

when the rare urine collection is completed, the cleaning device is turned on, and the interior of the toilet body is washed to clean residual urine of a patient, so as to reduce influence on urine samples collected by other patients who use the smart toilet, thereby collecting the urine samples more accurately.

For example, when washing and disinfecting the interior of the toilet body, disinfectant passes through the catheterization plate and the urine storage container in turn, and drained away through the pipeline and the catheterization pipeline, the present includes but is not limited thereto.

Figure 5:
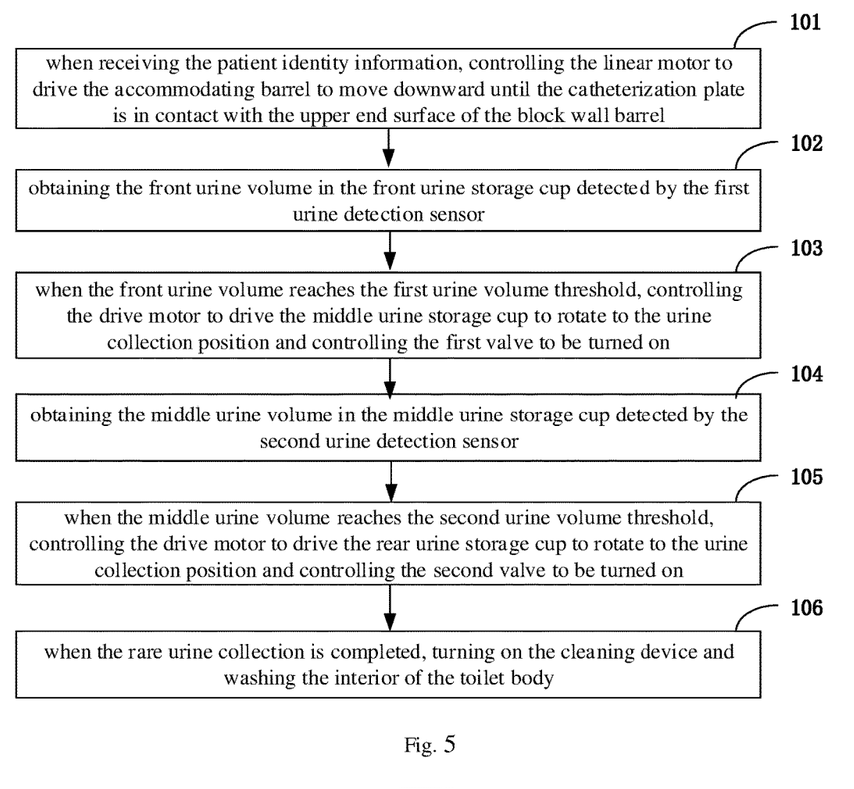
FIG. 5 is a flowing chart of an operation control method of a smart toilet provided by an embodiment of the present disclosure.

For example, FIG. 5 is a flow chart of an operation control method of a smart toilet provided by an embodiment of the present disclosure, as illustrated in FIG. 5, an example of the operation control method provided by the present disclosure includes the following steps 101-106.

Step 101, when receiving the patient identity information, controlling the linear motor to drive the accommodating barrel to move downward until the catheterization plate is in contact with the upper end surface of the block wall barrel.

Step 102, obtaining the front urine volume in the front urine storage cup detected by the first urine detection sensor.

Step 103, when the front urine volume reaches the first urine volume threshold, controlling the drive motor to drive the middle urine storage cup to rotate to the urine collection position and controlling the first valve to be turned on.

Step 104, obtaining the middle urine volume in the middle urine storage cup detected by the second urine detection sensor.

Step 105, when the middle urine volume reaches the second urine volume threshold, controlling the drive motor to drive the rear urine storage cup to rotate to the urine collection position and controlling the second valve to be turned on.

Step 106, when the rare urine collection is completed, turning on the cleaning device and washing the interior of the toilet body.

Figure 6:
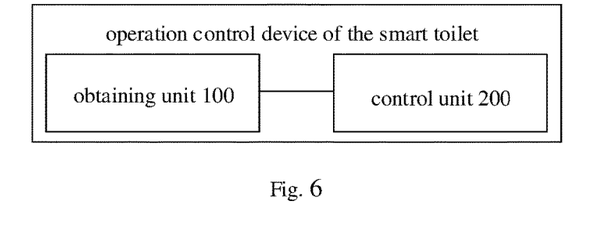
FIG. 6 is a structure view of an operation control device of a smart toilet provided by an embodiment of the present disclosure.

An embodiment of the present disclosure further provides an operation control device of the smart toilet as mentioned in above embodiments, as illustrated in FIG. 6, the operation control device of the smart toilet includes: an obtaining unit 100, configured to obtain front urine volume detected by the first urine detection sensor and middle urine volume detected by the second urine detection sensor; a control unit 200, configured to: when front urine volume in the first urine storage cup reaches the first urine volume threshold, control the drive motor to drive the middle urine storage cup to rotate to the urine collection position; when middle urine volume in the middle urine storage cup reaches the second urine volume threshold, control the drive motor to drive the rear urine storage cup to rotate to the urine collection position and control the second valve to be turned on.

In the operation control device of the smart toilet provided by the present disclosure, through controlling the drive motor to drive the urine storage container to rotate, so as to make the front urine storage cup, the middle urine storage cup and the rare urine storage cup locate in the urine collection position in turn and collect the front urine, the middle urine and the rare urine respectively, and turning on the second valve to transfer the middle urine into the urine cup as a urine detection sample for testing. Comparing with the prior art, the technical solution can collect the middle urine as the urine detection sample accurately, and improve convenience and health of the urine collection.

For example, the obtaining unit 100 and the control unit 200 may be implemented in software for execution by various types of processors. For example, in a case that the obtaining unit 100 and the control unit 200 may be implemented in software, considering a level of an existing hardware process, the obtaining unit 100 and the control unit 200 may be modules that can be implemented in software. Without considering the cost, a person having ordinary skill in the art may set up a corresponding hardware circuit to realize a corresponding function, the hardware circuit includes a conventional very-large-scale integration (VLSI) circuit or a field programmable gate array and an existing semiconductor such as a logic chip, a transistor, and the like, or other discrete components. For example, the control unit 200 may also be implemented with a programmable hardware device, such as a field programmable gate array, a programmable array logic, or a programmable logic device and so on, the present embodiment is not limited thereto.

For example, when receiving the patient identity information, the control unit 200 may be configured to control the linear motor to drive the accommodating barrel to move downward until the catheterization plate is in contact with the upper end surface of the block wall barrel.

For example, when the rare urine collection is completed, the control unit 200 is configured to turn on the cleaning device so as to wash the interior of the toilet body.

The above are only specific implementations of the present disclosure, and the scope of the present disclosure is not limited thereto, a person having ordinary skill in the art may make various modifications and variations to the disclosure without departing from the spirit and the scope of the disclosure. In this way, assuming that the modifications and the variations of the present disclosure fall within the scope of the claims of the present disclosure and their equivalents, the present disclosure is also intended to cover the modifications and the variations.

The present application claims priority to the Chinese patent application No. 201610634454.3 filed Aug. 5, 2016, the entire disclosure of which is incorporated herein by reference as part of the present application.

What is claimed is:

1. A smart toilet, comprising:
   a toilet body;
   a urine cup disposed outside the toilet body;
   a urine collection device disposed in the toilet body, comprising a rotation shaft and an urine storage container driven to be rotated by the rotation shaft, the urine storage container comprises a front urine storage cup, a middle urine storage cup and a rear urine storage cup distributed around the rotation shaft, the front urine storage cup is provided with a first urine detection sensor and a first valve, the middle urine storage cup is provided with a second urine detection sensor and a second valve; the front urine storage cup and the rear urine storage cup are connected with a catheterization pipeline of the smart toilet, the middle urine storage cup is connected with the urine cup through a pipeline;
   a drive motor, being in drive connection with the rotation shaft;
   a controller, electrically connected with the first urine detection sensor, the first valve, the second urine detection sensor, the second valve and the drive motor, and configured to control the drive motor to drive the middle urine storage cup to rotate to a urine collection position upon urine volume in the front urine storage cup reaching a first urine volume threshold, control the drive motor to drive the rear urine storage cup to rotate to the urine collection position and control the second valve to be turned on upon urine volume in the middle storage cup reaching a second urine volume threshold.

2. The smart toilet according to claim 1, wherein the first urine detection sensor and the first valve is provided at a bottom of the front urine storage cup, the second urine detection sensor and the second valve are provided at a bottom of the middle urine storage cup.

3. The smart toilet according to claim 1, further comprising:
   an accommodating barrel; and
   a funnel-shaped catheterization plate having a leak hole and located on a top of the accommodating barrel,
   wherein the urine collection device and the drive motor are located in the accommodating barrel, a position below the leak hole of the catheterization plate is the urine collection position.

4. The smart toilet according to claim 3, further comprising:
   a block wall barrel located outside the accommodating barrel and spaced from the accommodating barrel;
   a linear motor configured to drive the accommodating barrel to move up and down; and
   an information collection device configured to collect patient identity information,
   wherein the controller is electrically connected with the linear motor and the information collection device, and configured to control the linear motor to drive the accommodating barrel to move downward until the catheterization plate is in contact with an upper end surface of the block wall barrel upon receiving the patient identity information.

5. The smart toilet according to claim 4, wherein a position of the catheterization plate opposed to the upper end surface of the blocking wall barrel is provided with a seal strip.

6. The smart toilet according to claim 1, further comprising:
   a cleaning device configured to wash an interior of the toilet body,
   wherein the controller is electrically connected with the cleaning device, and configured to turn on the cleaning device upon rare urine collection being completed.

7. An operation control method of the smart toilet according claim 1, comprising:
   obtaining front urine volume in the front urine storage cup detected by the first urine detection sensor;
   when the front urine volume reaches the first urine volume threshold, controlling the drive motor to drive the middle urine storage cup to rotate to the urine collection position;
   obtaining middle urine volume in the middle urine storage cup detected by the second urine detection sensor;
   when the middle urine volume reaches the second urine volume threshold, controlling the drive motor to drive the rear urine storage cup to rotate to the urine collection position and controlling the second valve to be turned on.

8. The operation control method of the smart toilet according to claim 7, wherein the smart toilet further comprise: an accommodating barrel; and a funnel-shaped catheterization plate having a leak hole and located on a top of the accommodating barrel, the urine collection device and the drive motor are located in the accommodating barrel, a position below the leak hole of the catheterization plate is the urine collection position; the smart toilet further comprises a block wall barrel located outside the accommodating barrel and spaced from the accommodating barrel; a linear motor configured to drive the accommodating barrel to move up and down; and an information collection device configured to collect patient identity information, the controller is electrically connected with the linear motor and the information collection device, and configured to control the linear motor to drive the accommodating barrel to move downward until the catheterization plate is in contact with an upper end surface of the block wall barrel upon receiving the patient identity information, wherein the method further comprises:

when receiving the patient identity information, controlling the linear motor to drive the accommodating barrel to move downward until the catheterization plate is in contact with the upper end surface of the block wall barrel.

9. The operation control method of the smart toilet according to claim 7, wherein the smart toilet further comprises a cleaning device configured to wash an interior of the toilet body, the controller is electrically connected with the cleaning device, and configured to turn on the cleaning device upon rare urine collection being completed, wherein the method further comprises:

when the rare urine collection is completed, turning on the cleaning device and washing the interior of the toilet body.

10. An operation control device of the smart toilet according to claim 1, comprising:

an obtaining unit, configured to obtain front urine volume detected by the first urine detection sensor and middle urine volume detected by the second urine detection sensor;

a control unit, configured to when the front urine volume in the first urine storage cup reaches the first urine volume threshold, control the drive motor to drive the middle urine storage cup to rotate to the urine collection position;

when the middle urine volume in the middle urine storage cup reaches the second urine volume threshold, control the drive motor to drive the rear urine storage cup to rotate to the urine collection position and control the second valve to be turned on.

11. The operation control device of the smart toilet according to claim 10, wherein the smart toilet further comprise: an accommodating barrel; and a funnel-shaped catheterization plate having a leak hole and located on a top of the accommodating barrel, the urine collection device and the drive motor are located in the accommodating barrel, a position below the leak hole of the catheterization plate is the urine collection position; the smart toilet further comprises a block wall barrel located outside the accommodating barrel and spaced from the accommodating barrel; a linear motor configured to drive the accommodating barrel to move up and down; and an information collection device configured to collect patient identity information, the controller is electrically connected with the linear motor and the information collection device, and configured to control the linear motor to drive the accommodating barrel to move downward until the catheterization plate is in contact with an upper end surface of the block wall barrel upon receiving the patient identity information, wherein the control unit is configured to control the linear motor to drive the accommodating barrel to move downward until the catheterization plate is in contact with the upper end surface of the block wall barrel when receiving the patient identity information.

12. The operation control device of the smart toilet according to claim 10, wherein the smart toilet further comprises a cleaning device configured to wash an interior of the toilet body, the controller is electrically connected with the cleaning device, and configured to turn on the cleaning device upon rare urine collection being completed, wherein the control unit is configured to turn on the cleaning device so as to wash the interior of the toilet body when the rare urine collection is completed.

* * * * *